US012106846B2

(12) United States Patent
Taerum

(10) Patent No.: US 12,106,846 B2
(45) Date of Patent: Oct. 1, 2024

(54) SYSTEMS AND METHODS FOR HIGH BIT DEPTH RENDERING OF MEDICAL IMAGES IN A WEB BROWSER

(71) Applicant: Arterys Inc., San Francisco, CA (US)

(72) Inventor: Torin Taerum, Calgary (CA)

(73) Assignee: Arterys Inc., San Francisco, CA (US)

( * ) Notice: Subject to any disclaimer, the term of this patent is extended or adjusted under 35 U.S.C. 154(b) by 593 days.

(21) Appl. No.: 17/289,979

(22) PCT Filed: Nov. 15, 2019

(86) PCT No.: PCT/US2019/061671
§ 371 (c)(1),
(2) Date: Apr. 29, 2021

(87) PCT Pub. No.: WO2020/106569
PCT Pub. Date: May 28, 2020

(65) Prior Publication Data
US 2022/0005583 A1    Jan. 6, 2022

Related U.S. Application Data

(60) Provisional application No. 62/770,989, filed on Nov. 23, 2018.

(51) Int. Cl.
*G16H 30/20* (2018.01)
*G06F 16/957* (2019.01)
*G06T 7/00* (2017.01)

(52) U.S. Cl.
CPC ......... *G16H 30/20* (2018.01); *G06F 16/9577* (2019.01); *G06T 7/0012* (2013.01);
(Continued)

(58) Field of Classification Search
CPC .......................... G06F 16/9577; G06T 7/0012
See application file for complete search history.

(56) References Cited

U.S. PATENT DOCUMENTS 5,457,754 A * 10/1995 Han ........................... G06T 7/12
                                                                382/172
5,761,333 A *  6/1998 Hsieh ........................ G06T 5/94
                                                                382/131
(Continued)

FOREIGN PATENT DOCUMENTS

KR            101717457 B1      3/2017

OTHER PUBLICATIONS

International Search Report and Written Opinion, mailed Apr. 16, 2020, for International Application No. PCT/US2019/061671, 8 pages.
(Continued)

*Primary Examiner* — Kevin Ky
(74) *Attorney, Agent, or Firm* — Seed IP Law Group LLP

(57) ABSTRACT

Techniques to leverage computer monitor and graphics card hardware capabilities, using DCI-P3 and rec2020 color spaces for medical imagery are provided. The technique involves downloading the original raw source pixel data from the medical image from the webserver to the browser. A window and level transform is then applied to the raw pixel data enabling it to be displayed using the web browser capable of leveraging the hardware capabilities of commodity monitors and video cards that are capable of high bit depth display.

17 Claims, 4 Drawing Sheets

(52) U.S. Cl.
CPC .............. *G06T 2207/10081* (2013.01); *G06T 2207/10088* (2013.01); *G06T 2207/10101* (2013.01); *G06T 2207/10104* (2013.01); *G06T 2207/10108* (2013.01); *G06T 2207/30068* (2013.01)

(56) References Cited

U.S. PATENT DOCUMENTS

| | | | | |
|---|---|---|---|---|
| 8,494,301 | B2* | 7/2013 | Adams, Jr. | H04N 23/80 |
| | | | | 382/255 |
| 9,513,357 | B2 | 12/2016 | Hsiao et al. | |
| 10,117,597 | B2 | 11/2018 | Beckers et al. | |
| 10,331,852 | B2 | 6/2019 | Dormer et al. | |
| 2005/0100208 | A1* | 5/2005 | Suzuki | G06T 5/90 |
| | | | | 382/128 |
| 2006/0036625 | A1 | 2/2006 | Judd et al. | |
| 2008/0130839 | A1* | 6/2008 | Rogers | G06T 7/0012 |
| | | | | 378/207 |
| 2010/0141673 | A1* | 6/2010 | Gerade | G09G 5/10 |
| | | | | 345/589 |
| 2011/0205238 | A1* | 8/2011 | Wallace | G06T 5/92 |
| | | | | 345/589 |
| 2012/0045575 | A1 | 2/2012 | Thallner | |
| 2015/0011851 | A1 | 1/2015 | Mehta et al. | |
| 2016/0055634 | A1* | 2/2016 | Bystrov | G06T 5/50 |
| | | | | 382/128 |
| 2016/0064028 | A1 | 3/2016 | Uchimura et al. | |
| 2016/0064029 | A1 | 3/2016 | Zuckerman et al. | |
| 2016/0064031 | A1 | 3/2016 | Chin et al. | |
| 2016/0117411 | A1 | 4/2016 | Klotzer | |
| 2016/0350940 | A1 | 12/2016 | Wang | |
| 2020/0160978 | A1* | 5/2020 | Prosky | G06Q 10/06315 |
| 2021/0328113 | A1* | 10/2021 | Tydtgat | H01L 27/156 |

OTHER PUBLICATIONS

Beckers et al., "Apparatus, Methods and Articles for Four Dimensional (4D) Flow Magnetic Resonance Imaging," U.S. Appl. No. 61/928,702, filed Jan. 17, 2014. (106 pages).

Beckers et al., "Medical Imaging and Efficient Sharing of Medical Imaging Information," U.S. Appl. No. 62/260,565, filed Nov. 29, 2015. (67 pages).

De Francesco et al., "Medical Imaging, Efficient Sharing and Secure Handling of Medical Imaging Information," U.S. Appl. No. 62/501,613, filed May 4, 2017. (146 pages).

Dormer et al., "Medical Imaging and Efficient Sharing of Medical Imaging Information," U.S. Appl. No. 62/415,203, filed Oct. 31, 2016. (111 pages).

Golden et al., "Automated Cardiac Volume Segmentation," U.S. Appl. No. 62/415,666, filed Nov. 1, 2016. (119 pages).

Golden et al., "Automated Segmentation Utilizing Fully Convolutional Networks," U.S. Appl. No. 62/451,482, filed Jan. 27, 2017. (113 pages).

Golden et al., "Autonomous Detection of Medical Study Types," U.S. Appl. No. 62/589,833, filed Nov. 22, 2017. (177 pages).

Golden et al., "Content Based Image Retrieval for Lesion Analysis," U.S. Appl. No. 62/589,805, filed Nov. 22, 2017. (189 pages).

Golden et al., "Patient Outcomes Prediction System," U.S. Appl. No. 62/589,838, filed Nov. 22, 2017. (187 pages).

Hsiao et al., "Integrated Visualization and Quantitative Analysis Platform for Volumetric Phase-Contrast MRI," U.S. Appl. No. 61/571,908, filed Jul. 7, 2011. (16 pages).

Law et al., "Automated Three Dimensional Lesion Segmentation," U.S. Appl. No. 62/589,876, filed Nov. 22, 2017. (182 pages).

Leibowitz et al., "Systems and Methods for Interaction With Medical Image Data," U.S. Appl. No. 62/589,872, filed Nov. 22, 2017. (187 pages).

Lieman-Sifry et al., "Automated Lesion Detection, Segmentation, and Longitudinal Identification," U.S. Appl. No. 62/512,610, filed May 30, 2017. (87 pages).

Newton et al., "Three Dimensional Voxel Segmentation Tool," U.S. Appl. No. 62/589,772, filed Nov. 22, 2017. (180 pages).

Taerum et al., "Automated Lesion Detection, Segmentation, and Longitudinal Identification," U.S. Appl. No. 62/589,825, filed Nov. 22, 2017. (192 pages).

* cited by examiner

SYSTEMS AND METHODS FOR HIGH BIT DEPTH RENDERING OF MEDICAL IMAGES IN A WEB BROWSER

TECHNICAL FIELD

The present disclosure generally relates to medical imaging and particularly rendering medical imaging in a web browser.

BRIEF SUMMARY

Traditionally, diagnosis from medical images, such as mammography images, has required special hardware capable of displaying greater bit depth than commodity hardware has been capable of. More recently, commodity monitors and video cards are capable of high bit depth display. Described herein are techniques to leverage such computer monitor and graphics card hardware capabilities, using DCI-P3 and rec2020 color spaces for medical imagery. In medical imaging the brightness/contrast control is called the "window/level" control. The technique involves downloading the original raw source pixel data from the medical image from the webserver to the browser. A window and level transform is then applied to the raw pixel data enabling it to be displayed using the web browser capable of leveraging the hardware capabilities of commodity monitors and video cards that are capable of high bit depth display.

In one embodiment, a method of operating a processor-based system includes: obtaining, by at least one processor, raw pixel data from a medical image; receiving, by at least one processor, values indicative of window and level settings for the raw pixel data; applying, by at least one processor, a window and level transform to the raw pixel data based on the received values indicative of window and level settings for the raw pixel data; obtaining, by at least one processor, a result buffer based on the application of the window and level transform; generating, by at least one processor, an image data object based on the result buffer and optional parameters for color space and pixel format; and rendering, by at least one processor, an image in a web browser based on the generated image data object. The applying the transform may include mapping each pixel value of the raw pixel data to a value between 0 and 1 within a window defined by the window settings for the window and clamped outside the window.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with medical image capturing machines, computer systems, server computers, and/or communications networks have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are synonymous with "including," and are inclusive or open-ended (i.e., does not exclude additional, unrecited elements or method acts).

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
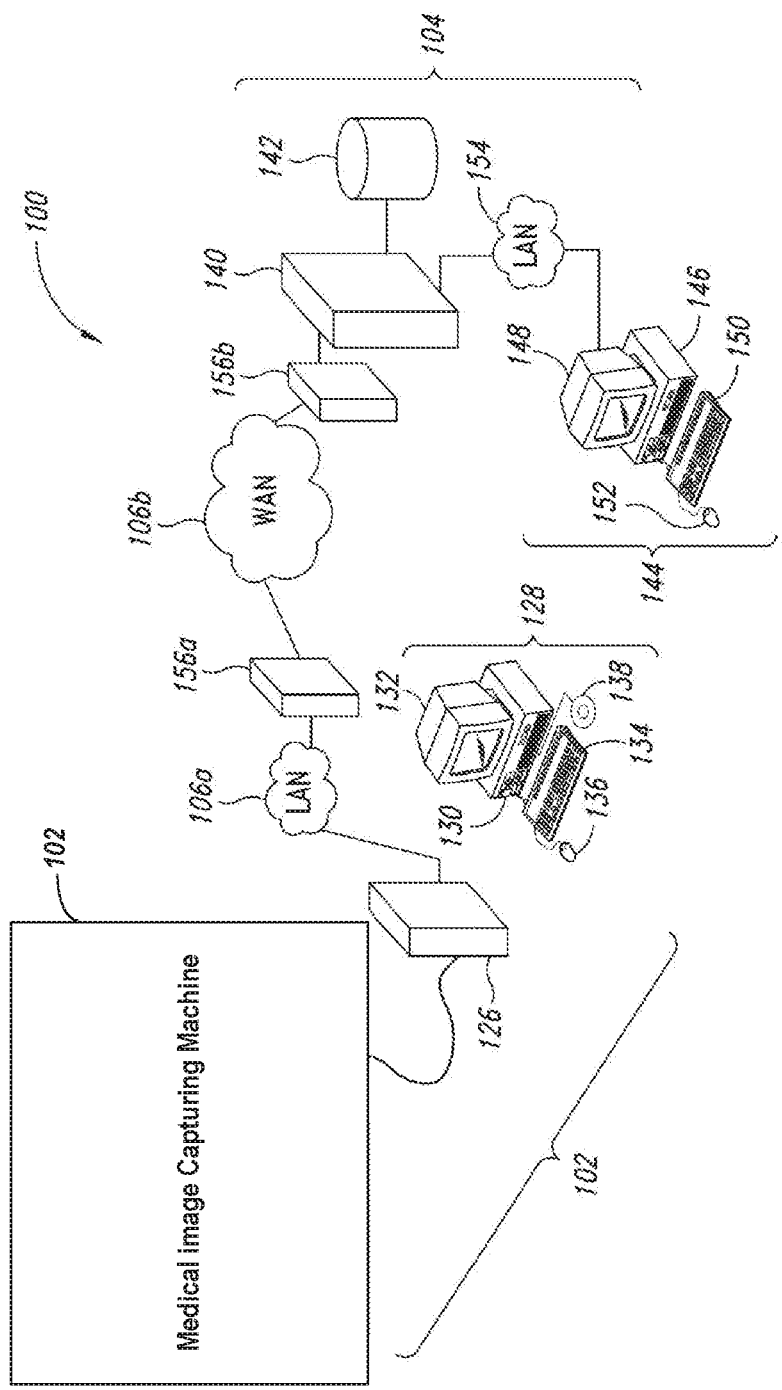
FIG. 1 is a schematic view of a networked environment including at least one medical image acquisition system and at least one image processing system, the medical image acquisition system located in a clinical setting and the image processing system located remotely from the medical image acquisition system and communicatively coupled therewith over one or more networks, according to one illustrated embodiment.

FIG. 1 shows a networked environment 100 according to one illustrated embodiment, in which one or more medical image acquisition systems (one shown) 102 are communicatively coupled to at least one medical image processing and display system 104 via one or more networks 106a, 106b (two shown, collectively 106).

The medical image acquisition system 102 is typically located at a clinical facility, for instance a hospital or dedicated medical imaging center. Examples of such medical acquisition systems include, but are not limited to: radiological imaging systems, medical x-ray imaging systems, mammography imaging systems, full-field digital mammography (FFDM) imaging systems, magnetic resonance imaging (MM) imaging systems, computerized tomography (CT) or computed axial tomography (CAT) imaging systems, ultrasound imaging systems, positron emission tomography (PET) imaging systems, single-photon emission computed tomography (SPECT or SPET) imaging systems, optical imaging systems and an optical coherence tomography (OCT) imaging systems. Various techniques and structures, as explained herein, may advantageously allow the image processing and display system 104 to be remotely located from the medical image acquisition system 102. The image processing and display system 104 may, for example, be located in another building, city, state, province or even country.

The medical image acquisition system 102 may, for example, include a medical image capturing machine 108, a computer system 110 and an operator's system 112. The medical image capturing machine 108.

The medical image capturing machine 108 typically includes, or is communicatively coupled to, a processor-based control system 126 used to control the medical image capturing machine 108. The processor-based control system 126 may include one or more processors, non-transitory computer- or processor-readable memory, drive circuitry and/or interface components to interface with the medical image capturing machine 108. The processor-based control system 126 may, in some implementations, also perform some preprocessing on data resulting from the medical imaging operation.

An operator's system 128 may include a computer system 130, monitor or display 132, keypad and/or keyboard 134, and/or a cursor control device such as a mouse 136, joystick, trackpad, trackball or the like. The operator's system 128 may include or read computer- or processor executable instructions from one or more non-transitory computer- or processor-readable medium, for instance media 138 such as flash memory, or a magnetic or optical disk. The operator's system 128 may allow a technician to operate the medical image capturing machine 108 to capture medical image data from a patient. Various techniques, structures and features described herein may allow medical image capturing machine 108 operation by a technician without requiring the presence of a clinician or physician. Such may advantageously significantly lower costs of medical imaging procedures. Also as described herein, various techniques, structures and features may allow medical image processing and display procedures to be performed much more quickly than using conventional techniques. For example, high computational power computers may be located remotely from the clinical setting, and may be used to serve multiple clinical facilities.

The image processing and display system 104 may include one or more servers to handle incoming requests and responses, and one or more rendering or image processing and display computers 140. The server(s) may, for example take the form of one or more server computers, workstation computers, supercomputers, or personal computers, executing server software or instructions. The one or more rendering or image processing and display computers 140 may take the form of one or more computers, workstation computers, supercomputers, or personal computers, executing image processing and/or analysis software or instructions. The one or more rendering or image processing and display computers 140 will typically employ one, and preferably multiple, graphical processing units (GPUs) or GPU cores.

The image processing and display system 104 may include one or more non-transitory computer-readable medium 142 (e.g., solid state hard drives, magnetic or optical hard drives, RAID, RAM, Flash) that stores processor-executable instructions and/or data or other information. The image processing and display system 104 may include one or more image processing and display operator's systems 144. The image processing and display operator's system 144 may include a computer system 146, monitor or display 148, keypad and/or keyboard 150, and/or a cursor control device such as a mouse 152, joystick, trackpad, trackball or the like. The image processing and display operator's system 144 may be communicatively coupled to the rendering or image processing and display computer(s) 140 via one or more networks, for instance a LAN 154. While many image processing techniques and analysis may be fully automated, the image processing and display operator's system may allow a technician to perform certain image processing and/or analysis operations on medical image data captured from a patient.

While illustrated as a single nontransitory computer- or processor-readable storage medium 142, in many implementations the nontransitory computer- or processor-readable storage medium 142 may constitute a plurality of nontransitory storage media. The plurality of nontransitory storage media may be commonly located at a common location, or distributed at a variety of remote locations. Thus, a database of raw medical image data, including raw pixel data, pre-processed medical image data and/or processed medical image data may be implemented in one, or across more than one, nontransitory computer- or processor-readable storage media. Such database(s) may be stored separately from one another on separate computer- or processor-readable storage medium 142 or may be stored on the same computer- or processor-readable storage medium 142 as one another. The computer- or processor-readable storage medium 142 may be co-located with the image processing and display system 104, for example, in the same room, building or facility. Alternatively, the computer- or processor-readable storage medium 142 may be located remotely from the image processing and display system 104, for example, in a different facility, city, state or country. Electronic or digital information, files or records or other collections of information may be stored at specific locations in non-transitory computer- or processor-readable media 142, thus are logically addressable portions of such media, which may or may not be contiguous.

As noted above, the image processing and display system 104 may be remotely located from the medical image acquisition system 102. The medical image capturing machine 102 and the image processing and display system 104 are capable of communications, for example via one or more communications channels, for example local area networks (LANs) 106a and Wide Area Networks (WANs) 106b. The networks 106 may, for instance include packet switched communications networks, such as the Internet, Worldwide Web portion of the Internet, extranets, and/or intranets. The networks 106 may take the form of various other types of telecommunications networks, such as cellular phone and data networks, and plain old telephone system (POTS) networks. The type of communications infrastructure should not be considered limiting.

As illustrated in FIG. 1, the medical image capturing machine 102 is communicatively coupled to the first LAN 106a. The first LAN 106a may be a network operated by or for the clinical facility, providing local area communications for the clinical facility. The first LAN 106a is communicatively coupled to the WAN (e.g., Internet) 106b. A first firewall 156a may provide security for the first LAN.

Also, as illustrated in FIG. 1, the image processing and display system 104 is communicatively coupled to the second LAN 154. The second LAN 154 may be a network operated by or for an image processing facility or entity, providing local area communications for the image processing facility or entity. The second LAN 154 is communicatively coupled to the WAN 106*b* (e.g., Internet). A second firewall 156*b* may provide security for the second LAN 154.

The image processing facility or entity, which may display high bit depth medical images on the monitor or display 148 of the operator's system 144 via a web browser running on the operator's system 144 may be independent from the clinical facility, for example an independent business providing services to one, two or many clinical facilities.

While not illustrated, the communications network may include one or more additional networking devices. The networking devices may take any of a large variety of forms, including servers, routers, network switches, bridges, and/or modems (e.g., DSL modem, cable modem), etc.

While FIG. 1 illustrates a representative networked environment 100, typical networked environments may include many additional medical image acquisition systems, image processing and display systems 104, computer systems, and/or entities. The concepts taught herein may be employed in a similar fashion with more populated networked environments than that illustrated. For example, a single entity may provide image processing and display services to multiple diagnostic entities. One or more of the diagnostic entities may operate two or more medical image acquisition systems 102. For example, a large hospital or dedicated medical imaging center may operate two, three or even more medical image acquisition systems at a single facility. Typically, the entity that provides the image processing and display services will operate multiple systems and provide image processing and display systems 104 which may include two, three or even hundreds of rendering or image processing and display computers 140 and operators' systems 144.

Figure 2:
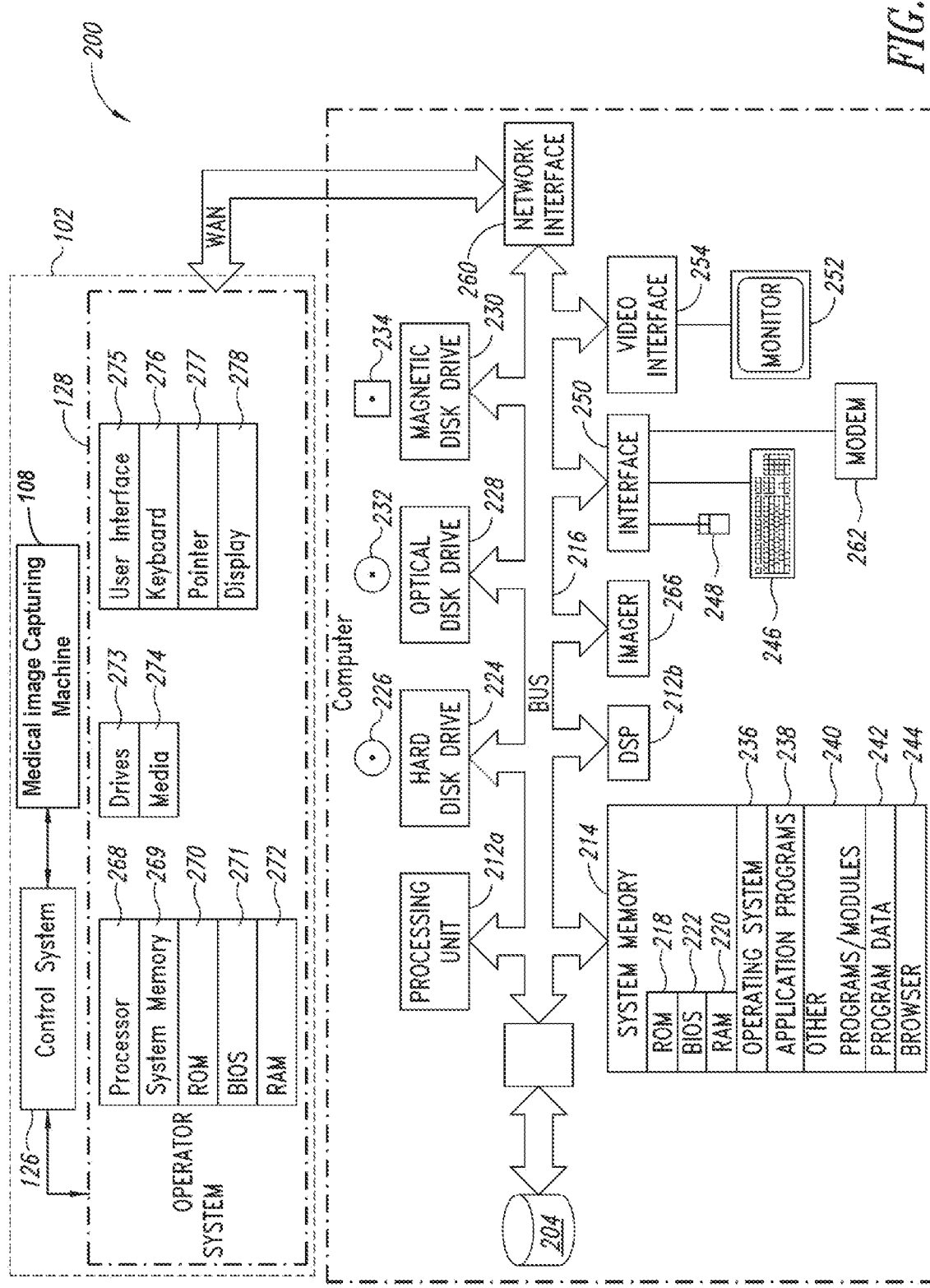
FIG. 2 is a functional block diagram of a medical image acquisition system and an image processing and display system that provides medical image processing and display services, according to one illustrated embodiment.

FIG. 2 shows a networked environment 200 comprising one or more image processing and display systems 104 (only one illustrated) and one or more associated nontransitory computer- or processor-readable storage medium 204 (only one illustrated). The associated nontransitory computer- or processor-readable storage medium 204 is communicatively coupled to the image processing and display system(s) 104 via one or more communications channels, for example, one or more parallel cables, serial cables, or wireless channels capable of high speed communications, for instance, via FireWire®, Universal Serial Bus® (USB) 2 or 3, and/or Thunderbolt®, Gigabyte Ethernet®.

The networked environment 200 also comprises one or more end medical image acquisition systems 102 (only one illustrated). The medical image acquisition system(s) 102 are communicatively coupled to the image processing and display system(s) 104 by one or more communications channels, for example, one or more wide area networks (WANs) 210, for instance the Internet or Worldwide Web portion thereof.

In operation, the medical image acquisition systems 102 may function as a client or server to the image processing and display system 104. In operation, the image processing and display systems 104 may function as a server or client to receive or send requests or information (e.g., medical image data sets) from or to the medical image acquisition systems 102. Described herein is an overall process which employs an asynchronous command and imaging pipeline that allows the image processing and display to be performed remotely (e.g., over a WAN) from the medical image acquisition system 102. This approach provides for a number of distinctive advantages, for instance allowing the medical image acquisition system(s) 102 to be operated by a technician without requiring the presence of a clinician (e.g., physician). Various techniques or approaches are also described to enhance security, while allowing access to medical imaging data as well as private patient specific health information.

While illustrated as located remotely from the medical image acquisition system(s) 102, in some implementations the image processing and display systems 104 may be co-located with the medical image acquisition system 102. In other implementations, one or more of the operations or functions described herein may be performed by the medical image acquisition system 102 or via a processor-based device co-located with the medical image acquisition system 102.

The image processing and display systems 104 receive medical image data sets, including raw pixel data, perform image processing on the medical image data sets, and provide the processed medical image data sets, for example, for display in a web browser, displays the processed medical image data sets, such as within a web browser and may provide the processed medical data image sets for review, such as to a clinician for review. The image processing and display systems 104 may, for example, perform transformations on the raw pixel data for display in a web browser, error detection and/or correction on medical data sets, for example phase error correction, phase aliasing detection, signal unwrapping, and/or detection and/or correction of various artifacts. Phase error is related to phase, as is phase aliasing. Signal unwrapping is related to magnitude. Various other artifacts may be related to phase and/or magnitude.

The image processing and display systems 104 may perform one or more of these operations or functions autonomously, without human input. Alternatively, the image processing and display systems 104 may perform one or more of these operations or functions based on human input, for example human input which identifies a point, location or plane, or which otherwise identifies a characteristic of anatomical tissue. The networked environment 200 may employ other computer systems and network equipment, for example, additional servers, proxy servers, firewalls, routers and/or bridges. The image processing and display systems 104 will at times be referred to in the singular herein, but this is not intended to limit the embodiments to a single device since in typical embodiments there may be more than one image processing and display systems 104 involved. Unless described otherwise, the construction and operation of the various blocks shown in FIG. 2 are of conventional design. As a result, such blocks need not be described in further detail herein, as they will be understood by those skilled in the relevant art.

The image processing and display systems 104 may include one or more processing units 212*a*, 212*b* (collectively 212), a system memory 214 and a system bus 216 that couples various system components, including the system memory 214 to the processing units 212. The processing units 212 may be any logic processing unit, such as one or more central processing units (CPUs) 212*a*, digital signal processors (DSPs) 212*b*, application-specific integrated circuits (ASICs), field programmable gate arrays (FPGAs), etc. The system bus 216 can employ any known bus structures or architectures, including a memory bus with memory controller, a peripheral bus, and/or a local bus. The system memory 214 includes read-only memory ("ROM") 218 and random access memory ("RAM") 220. A basic input/output system ("BIOS") 222, which can form part of the ROM 218, contains basic routines that help transfer information between elements within the image processing and display system(s) 104, such as during start-up.

The image processing and display system(s) 104 may include a hard disk drive 224 for reading from and writing to a hard disk 226, an optical disk drive 228 for reading from and writing to removable optical disks 232, and/or a magnetic disk drive 230 for reading from and writing to magnetic disks 234. The optical disk 232 can be a CD-ROM, while the magnetic disk 234 can be a magnetic floppy disk or diskette. The hard disk drive 224, optical disk drive 228 and magnetic disk drive 230 may communicate with the processing unit 212 via the system bus 216. The hard disk drive 224, optical disk drive 228 and magnetic disk drive 230 may include interfaces or controllers (not shown) coupled between such drives and the system bus 216, as is known by those skilled in the relevant art. The drives 224, 228 and 230, and their associated computer-readable media 226, 232, 234, provide nonvolatile storage of computer-readable instructions, data structures, program modules and other data for the image processing and display system(s) 104. Although the depicted image processing and display systems 104 is illustrated employing a hard disk 224, optical disk 228 and magnetic disk 230, those skilled in the relevant art will appreciate that other types of computer-readable media that can store data accessible by a computer may be employed, such as solid state drives, WORM drives, RAID drives, magnetic cassettes, flash memory cards, digital video disks ("DVD"), RAMs, ROMs, smart cards, etc.

Program modules can be stored in the system memory 214, such as an operating system 236, one or more application programs 238, other programs or modules 240 and program data 242. Application programs 238 may include instructions that cause the processor(s) 212 to perform image processing and display of medical images. For example, the application programs 238 may include instructions that cause the processor(s) 212 to perform application of transforms to raw pixel data representative of medical imagery for display via a web browser based on received values from an operator or other user indicative of window and level settings for the raw pixel data. The application programs 238 may also include instructions that cause the processor(s) 212 to perform obtaining a result buffer based on the application of the window and level transform, generating image data object based on the result buffer and optional parameters for color space and pixel format and rendering an image in a web browser based on the generated image data object.

The instructions may make use of sets or arrays of graphics processing units or GPUs to quickly render the visualizations.

Anatomical structure, represented as magnitude in the medical image data set, may, for example, be visualized using grey scale. Depth of view may be operator or user adjustable, for example via a slider control on a graphical user interface. Such may be based on patient specific input, for example provided by a technician, and may be based on the particular medical image capturing machine being used to capture the medical image MRI data set.

The application programs 238 may include instructions that cause the processor(s) 212 to receive image data sets from the medical image acquisition system, process, display and/or analyze the image data sets, and provide processed and/or analyzed images and other information to users remotely located from the image processing, in a time sensitive and secure manner. The system memory 214 may also include communications programs, for example, a browser 244 that causes the image processing and display system(s) 104 to display medical imagery downloaded via the Internet, intranets, extranets, telecommunications networks, or other networks as described below. The browser 244 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document. A number of suitable browsers may be commercially available such as those provided by Google, including those that are capable of leveraging computer monitor and graphics card hardware capabilities using DCI-P3 and ITU-R Recommendation BT.2020 (rec2020) color spaces.

In one embodiment, a technique to leverage computer monitor and graphics card hardware capabilities using DCI-P3 and rec2020 color spaces in the canvas2d context for a canvas tag for medical imagery, such as mammography images, is to download the original raw source pixel data from the medical image from the webserver to the browser 244. This data is typically 16 bit, but other high bit depth data may be used. When displaying the image the technician, operator or other user is given the ability to set a window and level for how the image is displayed. In medical imaging the brightness/contrast control is called the "window/level" control. A window and level transform is then applied to the raw pixel data. The window and level transform involves mapping each raw 16 bit pixel value to a value between 0 and 1 linearly within the window and clamped outside the window. One example of implementing such a transform is as follows, using a web browser that supports a 2D graphics API that can be used to create images on a web page:

```
function windowlevel(pixels, window_width, window_level) {
    var result = new Float32Array(pixels.length * 4);
    var subtrahend = window_level - window_width * 0.5;
    var multiplier = 1.0 / window_width;
    var j = 0;
    for(var i=0;i<pixels.length;++i,j+=4) {
        var t = (pixels[i] - subtrahend) * multiplier;
        if(t < 0.0) t = 0.0;
        if(t > 1.0) t = 1.0;
        result[j] = t;
        result[j+1] = t;
        result[j+2] = t;
        result[j+3] = 1.0;
    }
    return result;
}
```

The result buffer is then used in an ImageData object for a canvas2d context with the new optional parameters for color space and pixel format.

context.createImageData(result,width,height,{colorSpace:'P 3', pixelFormat:'float32'});

The canvas2d context that is used also uses new optional parameters:

context=canvas.getContext('2d', {colorSpace: 'P3', pixelFormat: 'float16'});

While shown in FIG. 2 as being stored in the system memory 214, the operating system 236, application programs 238, other programs/modules 240, program data 242 and server 244 can be stored on the hard disk 226 of the hard disk drive 224, the optical disk 232 of the optical disk drive 228 and/or the magnetic disk 234 of the magnetic disk drive 230.

An operator can enter commands and information into the image processing and display system(s) 104 through input devices such as a touch screen or keyboard 246 and/or a pointing device such as a mouse 248, and/or via a graphical user interface. Other input devices can include a microphone, joystick, game pad, tablet, scanner, etc. These and other input devices are connected to one or more of the processing units 212 through an interface 250 such as a serial port interface that couples to the system bus 216, although other interfaces such as a parallel port, a game port or a wireless interface or a universal serial bus ("USB") can be used. A monitor 252 or other display device is coupled to the system bus 216 via a video interface 254, such as a video adapter. The image processing and display system(s) 104 can include other output devices, such as speakers, printers, etc.

The image processing and display systems 104 can operate in a networked environment 200 using logical connections to one or more remote computers and/or devices. For example, the image processing and display 104 can operate in a networked environment 200 using logical connections to one or more medical image acquisition systems 102. Communications may be via a wired and/or wireless network architecture, for instance, wired and wireless enterprise-wide computer networks, intranets, extranets, and/or the Internet. Other embodiments may include other types of communications networks including telecommunications networks, cellular networks, paging networks, and other mobile networks. There may be any variety of computers, switching devices, routers, bridges, firewalls and other devices in the communications paths between the image processing and display systems 104, the medical image acquisition systems 102.

The medical image acquisition systems 102 will typically take the form of a medical image capturing machine 108 and one or more associated processor-based devices, for instance a control system 126 and/or operator's system 128. The medical image acquisition systems 102 capture medical image information or data sets from patients. Thus, in some instances the medical image acquisition systems 102 may be denominated as front end medical image acquisition systems or medical image capture systems, to distinguish such from the medical image processing and display system(s) 104, which in some instances may be denominated as medical image backend systems. The medical image acquisition systems 102 will at times each be referred to in the singular herein, but this is not intended to limit the embodiments to a single medical image acquisition system 102. In typical embodiments, there may be more than one medical image acquisition system 102 and there will likely be a large number of medical image acquisition systems 102 in the networked environment 200.

The medical image acquisition systems 102 may be communicatively coupled to one or more server computers (not shown). For instance, medical image acquisition systems 102 may be communicatively coupled via one or more diagnostic facility server computers (not shown), routers (not shown), bridges (not shown), LANs 106a (FIG. 1), etc., which may include or implement a firewall 156a (FIG. 1). The server computers (not shown) may execute a set of server instructions to function as a server for a number of medical image acquisition systems 102 (i.e., clients) communicatively coupled via a LAN 106a at a clinical facility or site, and thus act as intermediaries between the medical image acquisition systems 102 and the medical image processing and display system(s) 104. The medical image acquisition systems 102 may execute a set of client instructions to function as a client of the server computer(s) or as a server to client systems, which are communicatively coupled via a WAN.

The control system 126 typically includes one or more processor (e.g., microprocessors, central processing units, digital signal processors, graphical processing units) and non-transitory processor-readable memory (e.g., ROM, RAM, Flash, magnetic and/or optical disks). The operator's system 128 may take the form of a computer, for instance personal computers (e.g., desktop or laptop computers), net book computers, tablet computers, smart phones, personal digital assistants, workstation computers and/or mainframe computers, and the like, executing appropriate instructions.

The operator's system 128 may include one or more processing units 268, system memories 269 and a system bus (not shown) that couples various system components including the system memory 269 to the processing unit 268.

The processing unit 268 may be any logic processing unit, such as one or more central processing units (CPUs), digital signal processors (DSPs), application-specific integrated circuits (ASICs), field programmable gate arrays (FPGAs), graphical processing units (GPUs), etc. Non-limiting examples of commercially available computer systems include, but are not limited to, an 80×86 or Pentium series microprocessor from Intel Corporation, U.S.A., a PowerPC microprocessor from IBM, a Sparc microprocessor from Sun Microsystems, Inc., a PA-RISC series microprocessor from Hewlett-Packard Company, a 68xxx series microprocessor from Motorola Corporation, an ATOM processor, or an A4 or A5 processor. Unless described otherwise, the construction and operation of the various blocks of the medical image acquisition systems 102 shown in FIG. 2 are of conventional design. As a result, such blocks need not be described in further detail herein, as they will be understood by those skilled in the relevant art.

The system bus can employ any known bus structures or architectures, including a memory bus with memory controller, a peripheral bus, and a local bus. The system memory 269 includes read-only memory ("ROM") 270 and random access memory ("RAM") 272. A basic input/output system ("BIOS") 271, which can form part of the ROM 270, contains basic routines that help transfer information between elements within the medical image acquisition systems 102, such as during start-up.

The operator's system 128 may also include one or more media drives 273, e.g., a hard disk drive, magnetic disk drive, WORM drive, and/or optical disk drive, for reading from and writing to computer-readable storage media 274, e.g., hard disk, optical disks, and/or magnetic disks. The nontransitory computer-readable storage media 274 may, for example, take the form of removable media. For example, hard disks may take the form of a Winchester drive, and optical disks can take the form of CD-ROMs, while magnetic disks can take the form of magnetic floppy disks or diskettes. The media drive(s) 273 communicate with the processing unit 268 via one or more system buses. The media drives 273 may include interfaces or controllers (not shown) coupled between such drives and the system bus, as is known by those skilled in the relevant art. The media drives 273, and their associated nontransitory computer-readable storage media 274, provide nonvolatile storage of computer readable instructions, data structures, program modules and other data for medical image acquisition system(s) 102. Although described as employing computer-readable storage media 274 such as hard disks, optical disks and magnetic disks, those skilled in the relevant art will appreciate that operator's system(s) 128 may employ other types of nontransitory computer-readable storage media that can store data accessible by a computer, such as magnetic cassettes, flash memory cards, digital video disks ("DVD"), RAMs, ROMs, smart cards, etc. Data or information, for example, electronic or digital files or data or metadata related to such can be stored in the nontransitory computer-readable storage media 274.

An operator can enter commands and information into the operator's system(s) 128 via a user interface 275 through input devices such as a touch screen or keyboard 276 and/or a pointing device 277 such as a mouse. Other input devices can include a microphone, joystick, game pad, tablet, scanner, etc. These and other input devices are connected to the processing unit 269 through an interface such as a serial port interface that couples to the system bus, although other interfaces such as a parallel port, a game port or a wireless interface or a universal serial bus ("USB") can be used. A display or monitor 278 may be coupled to the system bus via a video interface, such as a video adapter. The operator system(s) 128 can include other output devices, such as speakers, printers, etc.

Program modules, such as an operating system, one or more application programs, other programs or modules and program data, can be stored in the system memory 269. Program modules may include instructions for accessing a Website, extranet site or other site or services (e.g., Web services) and associated Webpages, other pages, screens or services hosted or provided by the MM processing and analysis system(s) 104.

In particular, the system memory 269 may include communications programs that permit the medical image acquisition system(s) 102 to exchange electronic or digital information or files or data or metadata with the medical image processing and/or analysis services provided by the medical image processing and display system(s) 104. The communications programs may, for example, be a Web client or browser that permits the medical image acquisition system(s) 102 to access and exchange information, files, data and/or metadata with sources such as Web sites of the Internet, corporate intranets, extranets, or other networks. Such may require that an end user client have sufficient right, permission, privilege or authority for accessing a given Website, for example, one hosted by the medical image processing and display system(s) 104. The browser may, for example, be markup language based, such as Hypertext Markup Language (HTML), Extensible Markup Language (XML) or Wireless Markup Language (WML), and may operate with markup languages that use syntactically delimited characters added to the data of a document to represent the structure of the document.

Figure 3:
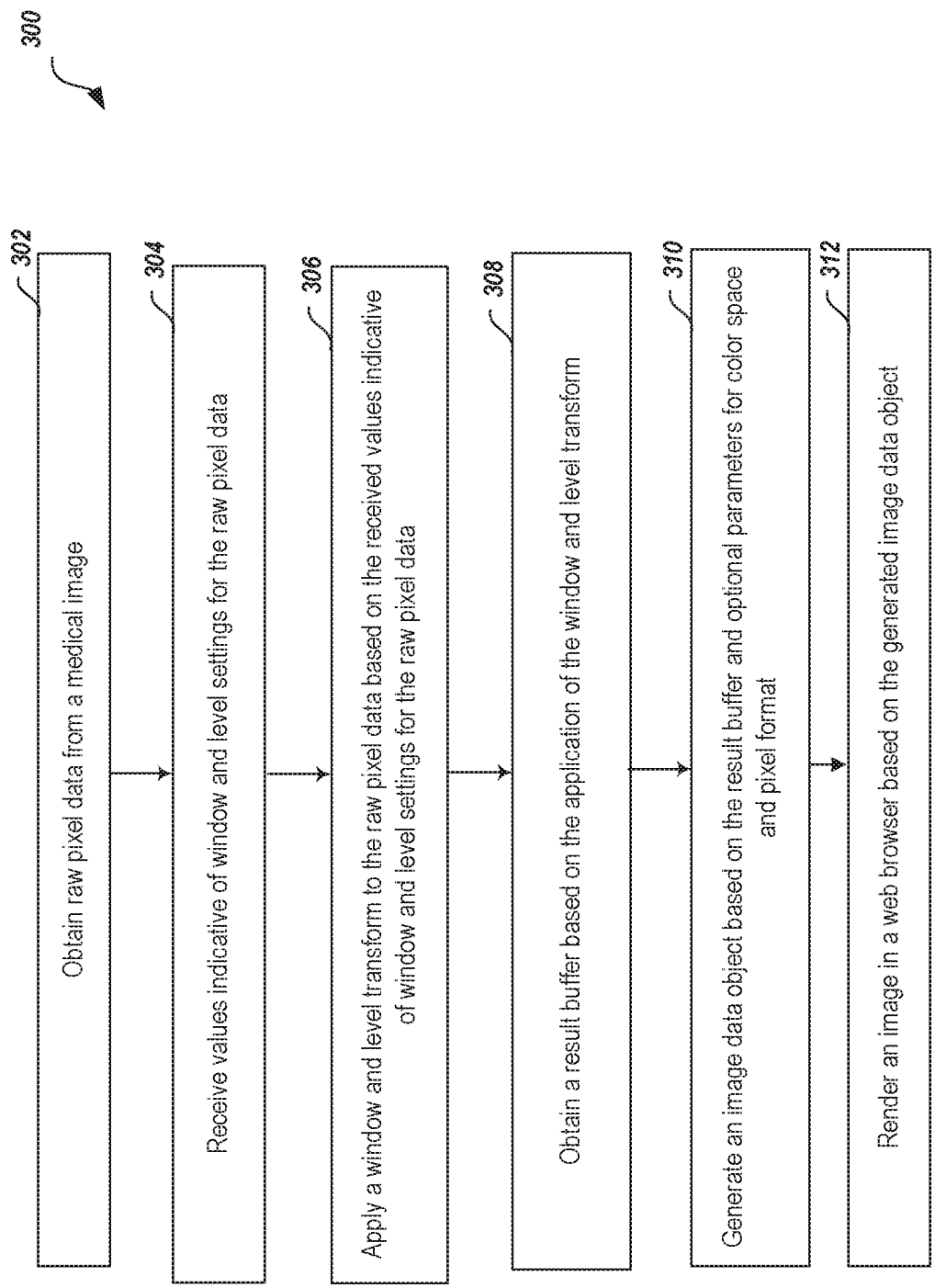
FIG. 3 is a flow diagram of an example process for rendering high bit depth medical images in a web browser, according to one illustrated embodiment.

FIG. 3 is a flow diagram of an example process 300 for rendering high bit depth medical images in a web browser. For example, the process 300 may be performed by the medical image acquisition system 102 and/or the medical image processing and display system 104.

At 302, the medical image processing and display system 104 obtains raw pixel data from a medical image;

At 304, the medical image processing and display system 104 receives values indicative of window and level settings for the raw pixel data;

At 306, the medical image processing and display system 104 applies a window and level transform to the raw pixel data based on the received values indicative of window and level settings for the raw pixel data.

At 308, the medical image processing and display system 104 obtains a result buffer based on the application of the window and level transform.

At 310, the medical image processing and display system 104 generates an image data object based on the result buffer and optional parameters for color space and pixel format.

At 312, the medical image processing and display system 104 renders an image in a web browser based on the generated image data object.

Figure 4:
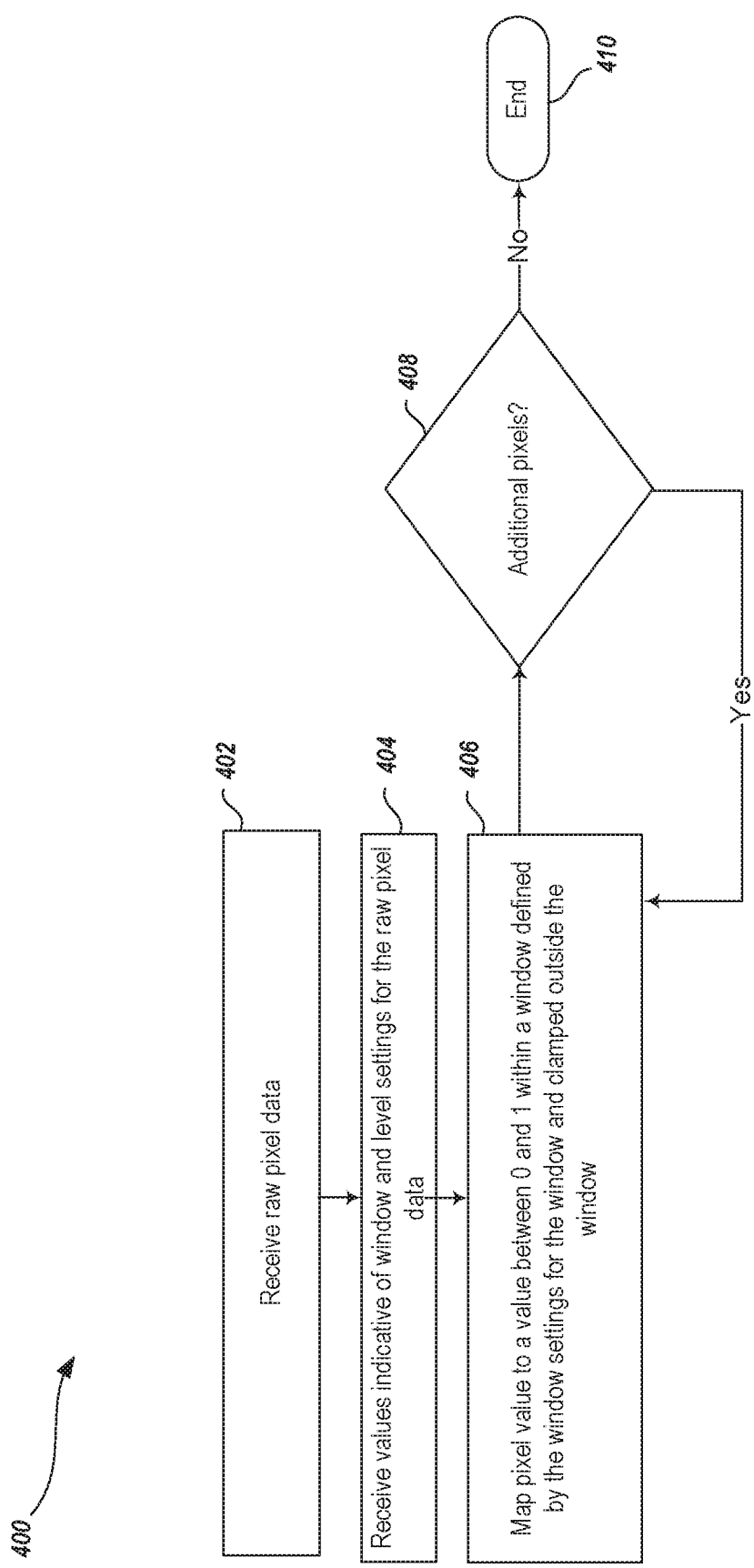
FIG. 4 is a flow diagram of an example process for processing raw pixel data useful in the process of FIG. 3 for rendering high bit depth medical images in a web browser, according to one illustrated embodiment.

FIG. 4 is a flow diagram of an example process for processing raw pixel data useful in the process of FIG. 3 for rendering high bit depth medical images in a web browser. For example, the process 400 may be performed by the medical image acquisition system 102 and/or the medical image processing and display system 104.

At 402, the medical image processing and display system 104 receives the raw pixel data from a medical image.

At 404, the medical image processing and display system 104 receives values indicative of window and level settings for the raw pixel data, such as from an operator or other user.

At 406, the medical image processing and display system 104 maps the pixel value to a value between 0 and 1 within a window defined by the window settings for the window and clamped outside the window.

At 408, the medical image processing and display system 104 determined whether there are additional pixels in the received raw pixel data to be processed for the medical image. If it is determined there are additional pixels in the received raw pixel data to be processed for the medical image, the process proceeds back to 404 to process the additional pixel.

If it is determined there are no additional pixels in the received raw pixel data to be processed for the medical image, the ends at 410.

The foregoing detailed description has set forth various implementations of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one implementation, the present subject matter may be implemented via Application Specific Integrated Circuits (ASICs). However, those skilled in the art will recognize that the implementations disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Those of skill in the art will recognize that many of the methods or algorithms set out herein may employ additional acts, may omit some acts, and/or may execute acts in a different order than specified.

In addition, those skilled in the art will appreciate that the mechanisms taught herein are capable of being distributed as a program product in a variety of forms, and that an illustrative implementation applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory.

The various implementations described above can be combined to provide further implementations. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 61/571,908 filed Jul. 7, 2011; U.S. Pat. No. 9,513,357 issued Dec. 6, 2016; PCT Patent Application No. PCT/US2012/045575 filed Jul. 5, 2012; U.S. patent application Ser. No. 15/363,683 filed Nov. 29, 2016; U.S. Provisional Patent Application No. 61/928,702 filed Jan. 17, 2014; U.S. patent application Ser. No. 15/112,130 filed Jul. 15, 2016; PCT Patent Application No. PCT/US2015/011851 filed Jan. 16, 2015; and U.S. Provisional Patent Application No. 62/260,565 filed Nov. 20, 2015; U.S. Provisional Patent Application No. 62/415,203 filed Oct. 31, 2016; PCT Patent Application No. US2016/064029 filed Nov. 29, 2016; PCT Patent Application No. US2016/064031 filed Nov. 29, 2016; U.S. Provisional Patent Application No. 62/415,666 filed Nov. 1, 2016; PCT Patent Application No. US2016/064028 filed Nov. 29, 2016; U.S. Provisional Patent Application No. 62/451,482 filed Jan. 27, 2017; U.S. Provisional Patent Application No. 62/501,613 filed May 4, 2017; U.S. Provisional Patent Application No. 62/512,610 filed May 30, 2017; U.S. Provisional Patent Application No. 62/589,825 filed Nov. 22, 2017; U.S. Provisional Patent Application No. 62/589,805 filed Nov. 22, 2017; U.S. Provisional Patent Application No. 62/589,772 filed Nov. 22, 2017; U.S. Provisional Patent Application No. 62/589,872 filed Nov. 22, 2017; U.S. Provisional Patent Application No. 62/589,876 filed Nov. 22, 2017; U.S. Provisional Patent Application No. 62/589,833 filed Nov. 22, 2017; U.S. Provisional Patent Application No. 62/589,838 filed Nov. 22, 2017, are incorporated herein by reference, in their entirety. Aspects of the implementations can be modified, if necessary, to employ systems, circuits and concepts of the various patents, applications and publications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

This application claims the benefit of priority to U.S. Provisional Application No. 62/770,989, filed Nov. 23, 2018, which application is hereby incorporated by reference in its entirety.

The invention claimed is:

1. A method comprising:
obtaining, by at least one processor, raw pixel data from a medical image;
receiving, by at least one processor, values indicative of window and level settings for the raw pixel data;
applying, by at least one processor, a window and level transform that at least (a) linearly maps each pixel value of the raw pixel data that falls within a window of pixel values to a respective value in a range between 0 and 1 and (b) clamps each pixel value of the raw pixel data that falls outside the window of pixel values, based on the received values indicative of window and level settings for the raw pixel data, wherein the window of pixel values is defined by the window and level settings;
obtaining, by at least one processor, a result buffer based on the application of the window and level transform;
generating, by at least one processor, an image data object based on the result buffer and optional parameters for color space and pixel format; and
rendering, by at least one processor, an image in a web browser based on the generated image data object.

2. The method of claim 1 further comprising:
enabling, by at least one processor, a user to input the values indicative of window and level settings to set a window and level for the raw pixel data for display of the medical image by the web browser.

3. The method of claim 1 wherein the optional parameters for color space and pixel format include the DCI-P3 color space.

4. The method of claim 1 wherein the optional parameters for color space and pixel format include the rec2020 color space.

5. The method of claim 1 wherein the medical image is an image generated by one or more of: radiological imaging systems, medical x-ray imaging systems, mammography imaging systems, full-field digital mammography (FFDM) imaging systems, magnetic resonance imaging (MRI) imaging systems, computerized tomography (CT) or computed axial tomography (CAT) imaging systems, ultrasound imaging systems, positron emission tomography (PET) imaging systems, single-photon emission computed tomography (SPECT or SPET) imaging systems, optical imaging systems and an optical coherence tomography (OCT) imaging systems.

6. The method of claim 1 wherein the medical image is a mammography image.

7. The method of claim 1 wherein the obtaining the raw source pixel data from a medical image includes downloading the raw source pixel to a web browser.

8. A system, comprising:
at least one nontransitory processor-readable storage medium that stores at least one of processor-executable instructions or data; and
at least one processor communicably coupled to the at least one nontransitory processor-readable storage medium, in operation the at least one processor implements a method comprising:
obtaining raw pixel data from a medical image;
receiving values indicative of window and level settings for the raw pixel data;
applying a window and level transform that at least (a) linearly maps each pixel value of the raw pixel data that falls within a window of pixel values to a respective value in a range between 0 and 1 and (b) clamps each pixel value of the raw pixel data that falls outside the window of pixel values, based on the received values indicative of window and level settings for the raw pixel data, wherein the window of pixel values is defined by the window and level settings;
obtaining a result buffer based on the application of the window and level transform;
generating an image data object based on the result buffer and optional parameters for color space and pixel format; and
rendering an image in a web browser based on the generated image data object.

9. The system of claim 8 wherein the method further comprises:
enabling, by at least one processor, a user to input the values indicative of window and level settings to set a window and level for the raw pixel data for display of the medical image by the web browser.

10. The system of claim 8 wherein the optional parameters for color space and pixel format include at least one of the DCI-P3 color space or the rec2020 color space.

11. The system of claim 8 wherein the medical image is an image generated by one or more of: radiological imaging systems, medical x-ray imaging systems, mammography imaging systems, full-field digital mammography (FFDM) imaging systems, magnetic resonance imaging (MRI) imaging systems, computerized tomography (CT) or computed axial tomography (CAT) imaging systems, ultrasound imaging systems, positron emission tomography (PET) imaging systems, single-photon emission computed tomography (SPECT or SPET) imaging systems, optical imaging systems and an optical coherence tomography (OCT) imaging systems.

12. The system of claim 8 wherein the medical image is a mammography image.

13. The system of claim 8 wherein the obtaining the raw source pixel data from a medical image includes downloading the raw source pixel to a web browser.

14. A nontransitory processor-readable storage medium having processor-executable instructions stored thereon that, when executed by at least one processor, cause the at least one computer processor to perform a method comprising:
obtaining raw pixel data from a medical image;
receiving values indicative of window and level settings for the raw pixel data;
applying a window and level transform that at least (a) linearly maps each pixel value of the raw pixel data that falls within a window of pixel values to a respective value in a range between 0 and 1 and (b) clamps each pixel value of the raw pixel data that falls outside the window of pixel values, based on the received values indicative of window and level settings for the raw pixel data, wherein the window of pixel values is defined by the window and level settings;
obtaining a result buffer based on the application of the window and level transform;
generating an image data object based on the result buffer and optional parameters for color space and pixel format; and
rendering an image in a web browser based on the generated image data object.

15. The storage medium of claim 14 wherein the method further comprises:
enabling, by at least one processor, a user to input the values indicative of window and level settings to set a window and level for the raw pixel data for display of the medical image by the web browser.

16. The storage medium of claim 14 wherein the optional parameters for color space and pixel format include at least one of the DCI-P3 color space or the rec2020 color space.

17. The storage medium of claim 14 wherein the medical image is an image generated by one or more of: radiological imaging systems, medical x-ray imaging systems, mammography imaging systems, full-field digital mammography (FFDM) imaging systems, magnetic resonance imaging (MRI) imaging systems, computerized tomography (CT) or computed axial tomography (CAT) imaging systems, ultrasound imaging systems, positron emission tomography (PET) imaging systems, single-photon emission computed tomography (SPECT or SPET) imaging systems, optical imaging systems and an optical coherence tomography (OCT) imaging systems.

* * * * *